United States Patent
Hartlieb et al.

(10) Patent No.: US 10,500,218 B2
(45) Date of Patent: Dec. 10, 2019

(54) UPTAKE OF PHARMACEUTICALS WITHIN CYCLODEXTRIN-BASED POROUS MATERIALS

(71) Applicants: Northwestern University, Evanston, IL (US); King Abdulaziz City for Science and Technology, Riyadh (SA)

(72) Inventors: Karel J. Hartlieb, Evanston, IL (US); James M. Holcroft, Newcastle upon Tyne (GB); James Fraser Stoddart, Evanston, IL (US); Daniel Patrick Ferris, Evanston, IL (US)

(73) Assignees: Northwestern University, Evanston, IL (US); King Abdulaziz City for Science and Technology, Riyadh (SA)

( * ) Notice: Subject to any disclaimer, the term of this patent is extended or adjusted under 35 U.S.C. 154(b) by 95 days.

(21) Appl. No.: 15/350,975

(22) Filed: Nov. 14, 2016

(65) Prior Publication Data

US 2017/0136128 A1  May 18, 2017

Related U.S. Application Data

(60) Provisional application No. 62/255,490, filed on Nov. 15, 2015, provisional application No. 62/416,334, filed on Nov. 2, 2016.

(51) Int. Cl.
| | | |
|---|---|---|
| A61K 31/616 | (2006.01) | |
| A61K 31/192 | (2006.01) | |
| A61K 47/69  | (2017.01) | |

(52) U.S. Cl.
CPC .......... *A61K 31/616* (2013.01); *A61K 31/192* (2013.01); *A61K 47/6951* (2017.08)

(58) Field of Classification Search
None
See application file for complete search history.

(56) References Cited

U.S. PATENT DOCUMENTS

| | | | |
|---|---|---|---|
| 9,085,460 B2 * | 7/2015 | Stoddart | ................ B01J 20/226 |
| 2003/0224006 A1 | 12/2003 | Zaworotko et al. | |
| 2014/0163111 A1 | 6/2014 | Rosi et al. | |
| 2015/0150981 A1 | 6/2015 | Gref et al. | |
| 2015/0322174 A1 | 11/2015 | Stoddart et al. | |
| 2016/0279263 A1 | 9/2016 | Putnam et al. | |

FOREIGN PATENT DOCUMENTS

| | | |
|---|---|---|
| WO | WO2014122105 | 8/2014 |
| WO | WO2015188199 | 12/2015 |
| WO | WO2016000032 | 1/2016 |

OTHER PUBLICATIONS

Hasan, Z., Choi, E. J., & Jhung, S. H. (2013). Adsorption of naproxen and clofibric acid over a metal-organic framework MIL-101 functionalized with acidic and basic groups. Chemical engineering journal, 219, 537-544. (Year: 2013).*

Forgan et al., Nanoporous Carbohydrate Metal-Organic Frameworks, J. Am. Chem. Soc., 134, Nov. 17, 2011, pp. 406-417.

Bernini et al., Screening of bio-compatible metal-organic frameworks as potential drug carriers using Monte Carlo simulations, J. Mater. Chem. B, 2, Nov. 25, 2013, pp. 766-774.

International Search Report and Written Opinion mailed in PCT Patent Application No. PCT/US2016/061963, dated Feb. 1, 2017.

Horcajada et al., Flexible Porous Metal-Organic Frameworks for a Controlled Drug Delivery, J. Am. Chem. Soc., 130, May 3, 2008, pp. 6774-6780.

Jambhekar et al., Cyclodextrins in pharmaceutical formulations I: structure and physicochemical properties, formation of complexes, and types of complex. *Drug Discov. Today,* Feb. 2016, vol. 21, pp. 356-362.

Jambhekar et al., Cyclodextrins in pharmaceutical formulations II: solubilization, binding constant, and complexation efficiency. *Drug Discov. Today,* Feb. 2016, vol. 21, pp. 363-368.

Horcajada et al., Metal-organic frameworks as efficient materials for drug delivery. *Angew. Chem. Int. Ed. 118,* Aug. 9, 2006, pp. 6120-6124.

Horcajada et al., Porous metal-organic-framework nanoscale carriers as a potential platform for drug delivery and imaging. *Nat. Mater.* Dec. 13, 2009, vol. 9, pp. 172-178.

Smaldone et al., Metal-Organic Frameworks from Edible Natural Products. *Angew. Chem., Int. Ed. 49,* Aug. 16, 2010, pp. 8630-8634.

Wu et al., Direct Calorimetric Measurement of Enthalpy of Adsorption of Carbon Dioxide on CD-MOF-2, a Green Metal-Organic Framework. *J. Am. Chem. Soc. 135,* Apr. 23, 2013, pp. 6790-6793.

Gassensmith et al., A Metal-Organic Framework-Based Material for Electrochemical Sensing of Carbon Dioxide. *J. Am. Chem. Soc. 136,* May 14, 2014, pp. 8277-8282.

(Continued)

*Primary Examiner* — Dale R Miller
(74) *Attorney, Agent, or Firm* — Quarles & Brady LLP; Tolga Gulmen

(57) ABSTRACT

Pharmaceutical complexes composed of drug molecules entrapped in cyclodextrin-based MOFs (CD-MOFs) are provided. Pharmaceutical tablets incorporating crystals of the pharmaceutical complexes for oral administration to a patient are also provided. In addition, methods of making the pharmaceutical complexes using anion-exchange reactions and methods of making the pharmaceutical complexes based on the co-crystallization of the drug molecules with cyclodextrin are provided. The pharmaceutical complexes include a CD-MOF and deprotonated drug anions associated with alkali metal cations in the CD-MOF superstructure.

19 Claims, 11 Drawing Sheets

(56) References Cited

OTHER PUBLICATIONS

Gassensmith et al., Strong and Reversible Binding of Carbon Dioxide in a Green Metal-Organic Framework. *J. Am. Chem. Soc. 133*, Aug. 30, 2011, pp. 15312-15315.
Han et al., A Metal-Organic Framework Stabilizes an Occluded Photocatalyst. *Chem. Eur. J. 19*, 2013, pp. 11194-11198.
Wei et al., Nanoparticle Core/Shell Architectures within MOF Crystals Synthesized by Reaction Diffusion. *Angew. Chem., Int. Ed. 51*, 2012, pp. 7435-7439.
Han et al., Tunneling Electrical Connection to the Interior of Metal-Organic Frameworks. *J. Am. Chem. Soc. 137*, May 28, 2015, pp. 8169-8175.
Furukawa et al., Nano- and Microsized Cubic Gel Particles from Cyclodextrin Metal-Organic Frameworks. *Angew. Chem., Int. Ed. 51*, 2012, pp. 10566-10569.
Holcroft et al., Carbohydrate-Mediated Purification of Petrochemicals. *J. Am. Chem. Soc. 137*, Mar. 25, 2015, pp. 5706-5719.
Hartlieb et al., CD-MOF: A Versatile Separation Medium. *J. Am. Chem. Soc. 138*, Jan. 27, 2016, pp. 2292-2301.
Yoon et al., Storage of electrical information in metal-organic-framework memristors, *Angew. Chem. Int. Ed. 53*, 2014, pp. 4437-4441.
Cai et al., Metal-Organic Framework-Based Nanomedicine Platforms for Drug Delivery and Molecular Imaging. *Small 11*, No. 2, Jul. 20, 2015, pp. 4806-4822.
Cunha et al., Rationalization of the entrapping of bioactive molecules into a series of functionalized porous zirconium terephthalate MOFs., *J. Mater. Chem. B 1*, Jan. 14, 2013, pp. 1101-1108.
Silva et al., Enhanced performance of a metal-organic framework analogue to MIL-101(Cr) containing amine groups for ibuprofen and nimesulide controlled release. *Inorg. Chem. Commun. 70*, May 21, 2016, pp. 47-50.
Cheng et al., Integrated Nanozymes with Nanoscale Proximity for in Vivo Neurochemical Monitoring in Living Brains. *Anal. Chem. 88*, Apr. 12, 2016, pp. 5489-5497.
Zhang et al., Metal-Organic-Framework-Based Vaccine Platforms for Enhanced Systemic Immune and Memory Response. *Adv. Funct. Mater. 26*, Jul. 19, 2016, pp. 6454-6461.
Simon-Yarza et al., In vivo behavior of MIL-100 nanoparticles at early times after intravenous administration. *Int. J. Pharm. 511*, Aug. 8, 2016, pp. 1042-1047.
Zheng et al., One-Step Synthesis of Nanoscale Zeolitic Imidazolate Frameworks with High Curcumin Loading for Treatment of Cervical Cancer. *ACS Appl. Mater. Interfaces 7*, Sep. 25, 2015, pp. 22181-22187.
He et al., $Fe_3O_4$@carbon@zeolitic imidazolate framework-8 nanoparticles as multifunctional pH-responsive drug delivery vehicles for tumor therapy in vivo., *J. Mater. Chem. B 3*, Oct. 20, 2015, pp. 9033-9042.
Bueno-Perez et al., Enantioselective adsorption of ibuprofen and lysine in metal-organic frameworks. *Chem. Commun. 50*, Jul. 24, 2014, pp. 10849-10852.
Bernini et al., Supporting Information for: Screening of biocompatible metal-organic frameworks as potential drug carriers using Monte Carlo simulations, Electronic Supplementary Material (ESI) for Journal of Materials Chemistry B (2014).

\* cited by examiner

US 10,500,218 B2

UPTAKE OF PHARMACEUTICALS WITHIN CYCLODEXTRIN-BASED POROUS MATERIALS

CROSS-REFERENCE TO RELATED APPLICATIONS

The present application claims priority to U.S. provisional patent application No. 62/255,490 that was filed on Nov. 15, 2015, and to U.S. provisional patent application No. 62/416,334 that was filed on Nov. 2, 2016, the entire contents of both of which are hereby incorporated by reference.

BACKGROUND

The development of new formulations that enhance water solubility and bioavailability of active pharmaceutical ingredients (APIs) is an important area of modern drug delivery, given that a large number of highly active potential drug candidates are relatively hydrophobic in nature. Additionally, oral administration routes are highly preferred, as they lead to increased patient compliance and avoid needles/pain and the need for sterile conditions during formulation manufacture. Numerous types of oral formulations have been proposed in order to overcome the obstacles related to poor bioavailability of hydrophobic APIs. These formulations use (i) micelles, (ii) micro/nano-emulsions, (iii) liposomes, (iv) dendrimers, (v) biodegradable polymer and mesoporous silica nanoparticles, and (vi) water-soluble excipients such as cyclodextrins, among others.

Ibuprofen is a widely available and moderately potent non-steroidal anti-inflammatory drug (NSAID) that has a low systemic toxicity and, unlike some other NSAIDs, such as aspirin, indomethacin and piroxicam, has a relatively low risk of side effects related to gastric damage. This API has been entrapped in a variety of metal organic frameworks (MOFs), including UiO-66 that had been modified with a variety of functional groups resulting in loading ranges from 13 to 36 weight percent (wt. %); MIL-53(Cr) and MIL-53 (Fe) that show loading capacities of around 20 wt. %; MIL-101(Cr) and 10% $NH_2$-MIL-101(Cr) with loadings of 46 and 47 wt. %, respectively; and MIL-100 and MIL-101 with ibuprofen loadings of 26 and 58 wt. %, respectively. (See, Cunha, D.; Gaudin, C.; Colinet, I.; Horcajada, P.; Maurin, G.; Serre, C., Rationalization of the entrapping of bioactive molecules into a series of functionalized porous zirconium terephthalate MOFs. *J. Mater. Chem. B* 2013, 1, 1101-1108; Silva, I. M. P.; Carvalho, M. A.; Oliveira, C. S.; Profirio, D. M.; Ferreira, R. B.; Corbi, P. P.; Formiga, A. L. B., Enhanced performance of a metal-organic framework analogue to MIL-101(Cr) containing amine groups for ibuprofen and nimesulide controlled release. *Inorg. Chem. Commun.* 2016, 70, 47-50; Horcajada, P.; Serre, C.; Vallet-Regi, M.; Sebban, M.; Taulelle, F.; Ferey, G., Metal-organic frameworks as efficient materials for drug delivery. *Angew. Chem. Int. Ed.* 2006, 45, 5974-5978; and Horcajada, P.; Serre, C.; Maurin, G.; Ramsahye, N. A.; Balas, F.; Vallet-Regi, M.; Sebban, M.; Taulelle, F.; Ferey, G., Flexible porous metal-organic frameworks for a controlled drug delivery. *J. Am. Chem. Soc.* 2008, 130, 6774-6780.) Few studies, however, have considered the use of MOFs in vivo, as a consequence of the toxic nature of the metal ions and/or organic linkers, and the investigations that have considered in vivo activity focus mainly on intraveneous, rather than oral, dosing as a result of the poor water-solubility of the MOFs that were used.

SUMMARY

Pharmaceutical complexes composed of drug molecules entrapped in cyclodextrin-based MOFs (CD-MOFs), methods of making the pharmaceutical complexes using anion-exchange reactions, and methods of making the pharmaceutical complexes based on the co-crystallization of the drug molecules with γ-cyclodextrin (γ-CD) are provided.

One example of a pharmaceutical complex comprises: a metal organic framework comprising γ-cyclodextrin tori coordinated to alkali metal cations on primary and secondary faces of the γ-cyclodextrin tori; and deprotonated drug molecules associated with the alkali metal cations as charge-balancing anions. In this pharmaceutical complex, the drug molecule may have a loading of at least 10 wt. %, including at least 20 wt. %. The CD-MOF in some embodiments of this pharmaceutical complex is CD-MOF-1, CD-MOF-2, or an offset channel metal organic framework comprising γ-cyclodextrin tori linked to one another through the alkali metal cations to form channels that are stacked in an offset manner down the crystallographic a-axis of the metal organic framework and has the chemical formula $C_{96}H_{169}X_3O_{84.5}$, $3H_2O$, where X is an alkali metal element, and crystallizes in the P1 space group. In some embodiments of this pharmaceutical complex, the deprotonated drug molecules are deprotonated ibuprofen molecules, deprotonated naproxen molecules, or deprotonated aspirin molecules.

One embodiment of a method of forming a pharmaceutical complex comprises: forming a solution comprising the free-acid form of acidic drug molecules and metal organic frameworks in a water-soluble, polar organic solvent, wherein the metal organic frameworks comprise γ-cyclodextrin tori coordinated to alkali metal cations on primary and secondary faces of the γ-cyclodextrin tori and further comprises charge compensating anions associated with the alkali metal cations, and further wherein the polar organic solvent facilitates the deprotonation of the free-acid form of the acidic drug molecules; and allowing the deprotonated acidic drug molecules to undergo anion exchange with the charge compensating anions of the metal organic frameworks to form metal organic frameworks loaded with deprotonated acidic drug molecules. The CD-MOF used in some embodiments of this method is CD-MOF-1, CD-MOF-2, or an offset channel metal organic framework comprising γ-cyclodextrin tori linked to one another through the alkali metal cations to form channels that are stacked in an offset manner down the crystallographic a-axis of the metal organic framework and has the chemical formula $C_{96}HJ_{169}X_3O_{84.5}$, $3H_2O$, where X is an alkali metal element, and crystallizes in the P1 space group. In some embodiments of this method, the deprotonated drug molecules are deprotonated ibuprofen molecules, deprotonated naproxen molecules, or deprotonated aspirin molecules.

Another method of forming a pharmaceutical complex comprises: forming a solution comprising an alkali metal salt of a drug molecule, γ-cyclodextrin, and an organic alcohol; and co-crystallizing the alkali metal salt of the drug molecule and the γ-cyclodextrin in the presence of the organic alcohol to form a metal organic framework comprising γ-cyclodextrin tori coordinated to alkali metal cations on primary and secondary faces of the γ-cyclodextrin tori, wherein the drug molecules are associated with the alkali metal cations as charge-balancing anions. The CD-MOF formed in some embodiments of this method is CD-MOF-1, CD-MOF-2, or an offset channel metal organic framework comprising γ-cyclodextrin tori linked to one another through the alkali metal cations to form channels that are stacked in an offset manner down the crystallographic a-axis of the metal organic framework and has the chemical formula $C_{96}H_{169}X_3O_{84.5}$, $3H_2O$, where X is an alkali metal element, and crystallizes in the P1 space group. In some embodiments of method, the drug molecules are deprotonated ibuprofen molecules, deprotonated naproxen molecules, or deprotonated aspirin molecules.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

Figure 1A:
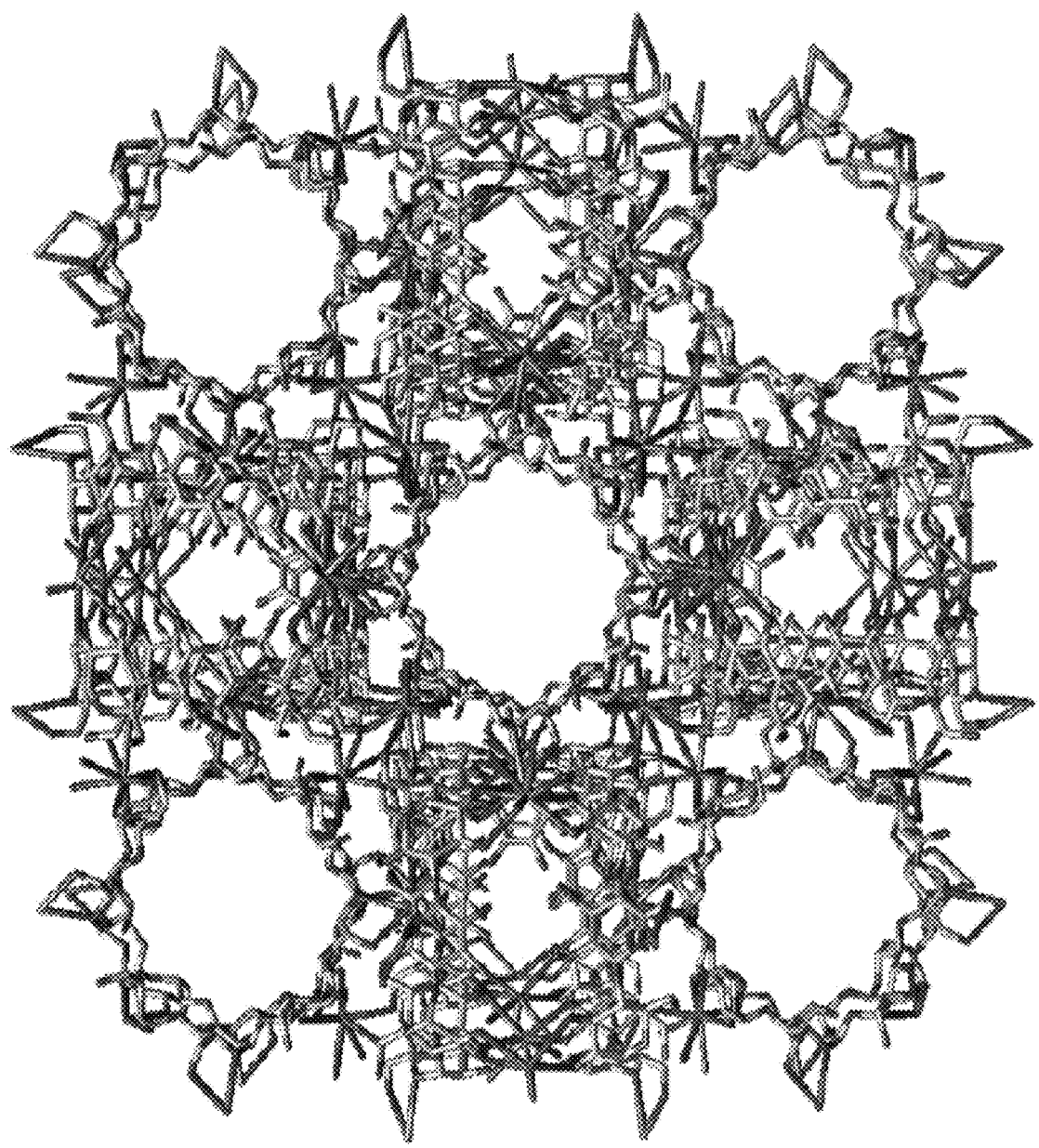
FIG. 1A depicts the solid-state structure of CD-MOF-1.

Pharmaceutical complexes composed of drug molecules entrapped in cyclodextrin-based MOFs (CD-MOFs) are provided. Pharmaceutical tablets incorporating crystals of the pharmaceutical complexes for oral administration to a patient are also provided. In addition, methods of making the pharmaceutical complexes using anion-exchange reactions and methods of making the pharmaceutical complexes based on the co-crystallization of the drug molecules with γ-cyclodextrin (γ-CD) are provided.

The pharmaceutical complexes include a CD-MOF and deprotonated drug anions associated with alkali metal cations in the CD-MOF superstructure. The porous nature of the CD-MOFs and the ease with which the porosity of these materials can be modified facilitate the incorporation of pharmaceutically active anions within their extended structures at high loadings. Embodiments of the pharmaceutical complexes can increase the half-life of the drug molecules in blood plasma relative to pure salt forms of the drug molecules, without significantly affecting their bioavailability and uptake. Thus, the complexes can be used as delivery agents for drugs, such as NSAIDs, to provide rapid pain relief and an extended duration of the analgesic effect. Embodiments of the pharmaceutical complexes can also enhance the stability of the entrapped drug molecules against degradation by atmospheric water vapor, making it possible to deliver the drugs in an oral tablet form. This is particularly significant for drugs having a pure salt form that is unstable in atmospheric moisture, such as the potassium salt of ibuprofen.

Metal-organic frameworks (MOFs) are a class of hybrid materials comprising inorganic nodes and organic linkers. More specifically, the MOFs have a structure comprising inorganic (e.g., metal) nodes, also referred to as centers, coordinated via organic molecular linkers to form a highly connected porous network. The CD-MOFs are porous materials constructed from CD-based organic molecular linker coordinated by alkali metal cation nodes. The CD tori have a macrocyclic nature, which is composed of a central lipophilic cavity and a hydrophilic outer surface, in addition to a truncated cone or 'bucket' shape having a primary face and a secondary face. The CD-MOFs built from the CD tori are generally characterized by larger cavities connected be a series of smaller channel-like pores. Charge-balancing counterions are present in the CD-MOF structures to compensate for the metal cation nodes. The charge balancing anions that are initially present in the CD-MOFs are derived from the salts used to synthesize the CD-MOFs. For example, if the CD-MOFs are crystallized from a metal hydroxide, the charge-balancing anions will be hydroxy (-OH) anions, while a CD-MOF crystallized using a metal benzoate will have benzoate anions as charge-balancing counterions. In some embodiments of the CD-MOFs, as discussed in more detail below, it is the anionic drug molecules themselves that serve as the initial charge balancing anions.

The CD-MOFs are highly water soluble, non-toxic and, given that they can be constructed from biocompatible CD and biocompatible metals, they also possess properties that are favorable for the development of oral drug formulations. Additionally, γ-CD can be hydrolyzed by salivary α-amylase, whereas α- and β-CD are essentially stable but are instead digested by intestinal microflora, which enables drug formulations based on the CD-MOFs to be adopted for fast-dispersing dosing.

Figure 1B:
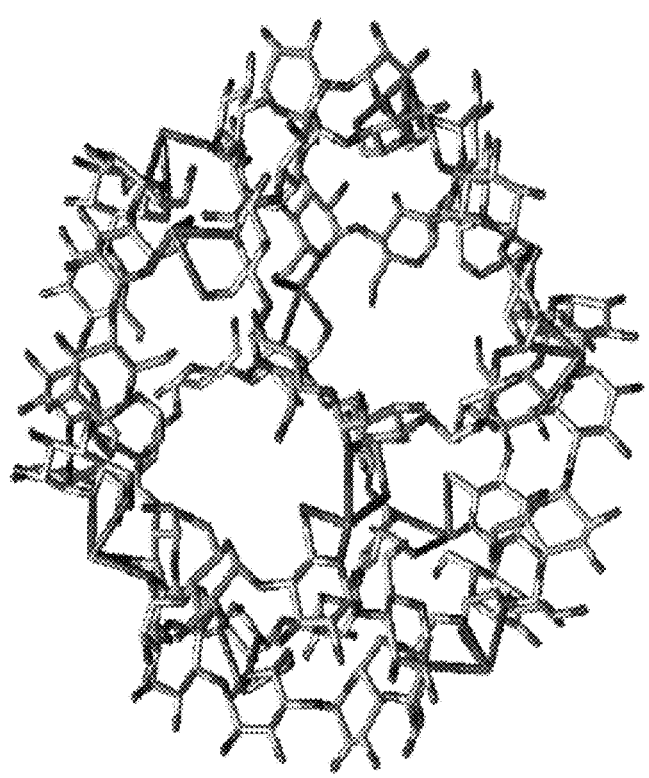
FIG. 1B depicts the structural formula of CD-MOF-1 revealing the coordination of potassium ions on a single γ-CD macrocycle.

Examples of γ-CD-based CD-MOFs in which anionic drug molecules can be entrapped are CD-MOF-1; CD-MOF-2; and CD-MOF-3. The structures of these CD-MOFs are described in detail in Forgan et al., *J. Am. Chem. Soc.* 2012, 134, 406-417. The structure of CD-MOF-1 is shown in FIGS. 1(A) and 1(B). This porous structure is based upon six γ-CD tori that are coordinated to potassium cations on the primary face of the CD tori in an alternating manner, forming cubes. These cubes are linked together in 3 dimensions by coordination of a potassium cation on the secondary face of the γ-CD tori, leading to an extended porous superstructure. CD-MOF-2 and CD-MOF-3 are isostructural with CD-MOF-1, but comprise rubidium and cesium nodes, respectively, rather than potassium nodes. These CD-MOFs define cavities with diameters of about 1.7 nm and channels with diameters of about 0.8 nm. The drug molecules can also be entrapped by CD-MOF-4, which is also described in Forgan et al., *J. Am. Chem. Soc.* 2012, 134, 406-417. However, since CD-MOF-3 and CD-MOF-4 have Cs nodes, they may be disfavored for drug delivery applications.

Other examples of CD-MOFs that can be used in the pharmaceutical complexes are referred to herein as offset channel structure CD-MOFs. These CD-MOFs are characterized by organic linkers of cyclodextrin tori linked to one another through alkali metal cations to form channels that are stacked in an offset manner down the crystallographic a-axis of the metal organic framework. The structure of one embodiment of an offset channel structure CD-MOFs is similar to the solid state structure $[(NaOH)_2 \cdot (\gamma\text{-}CD)]_n$ described in Forgan et al, but with sodium coordinated to the primary faces of γ-CDs to complete the MOF superstructure. An embodiment of an offset channel structure MOF is described in Example 3 and shown in FIG. 7. This framework has the chemical formula $C_{96}H_{169}Na_3O_{84.5}$, $3H_2O$, and crystallizes in the P1 space group, with unit cell dimensions of $\alpha=15.1647(8)$, $b=16.8291(9)$, $c=17.0271(9)$ Å, $\alpha=90.919(3)$, $\beta=97.999(3)$, $\gamma=97.116(3)°$, with a cell volume of 4267.58 Å$^3$. Other offset channel structure CD-MOFs that are isostructural with the CD-MOF in FIG. 7, but have different alkali metals, such as potassium, at their nodes can also be used.

The drug molecules that are incorporated into the CD-MOFs are active pharmaceutical ingredients in the form of small organic anions. Drug molecules that are incorporated into the CD-MOF superstructure by anion exchange are acids that can be deprotonated to provide charge-balancing counterions for the CD-MOFs and are desirably small enough to fit inside the channels of the CD-MOF structure. For example, the drug molecules are desirably small enough to fit into a channel having a diameter of 1.5 nm or smaller, including a channel having a diameter of 1 nm or smaller. Drug molecules that are incorporated into the CD-MOF superstructure by co-crystallization with the CD can be provided as alkali metal halide acid salts of the active pharmaceutical ingredient, such that their alkali metal cations provide the metal source for the crystallization of the alkali metal nodes of the CD-MOFs. These drug molecules are also desirably small enough to fit inside the channels of the CD-MOF structure. However, larger drug molecules can also be used, provided they are small enough to fit within the larger MOF cavities. By way of illustration, drug molecules able to fit into cavities with diameters in the range from about 1 to about 2.5 nm can be used, including drug molecules able to fit into cavities with diameters in the range from about 1.5 to about 2 nm.

Figure 1C:
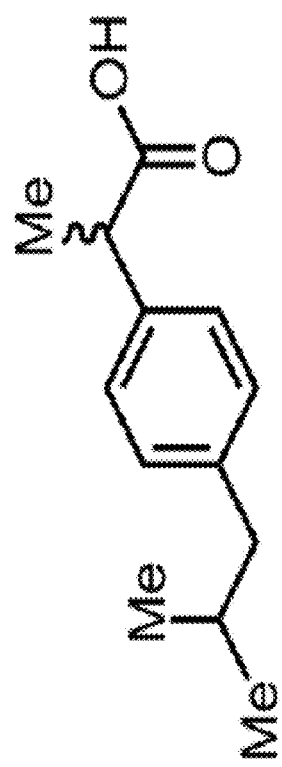
FIG. 1C shows the structural formula of ibuprofen.
Figure 6:
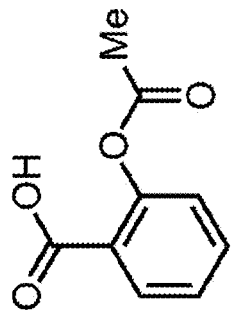
FIG. 6 shows the structures of the drug molecules naproxen, aspirin, diclofenac, and zidovudine.
Figure 6:
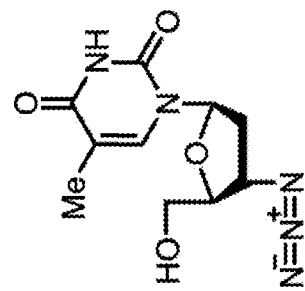
Figure 6:
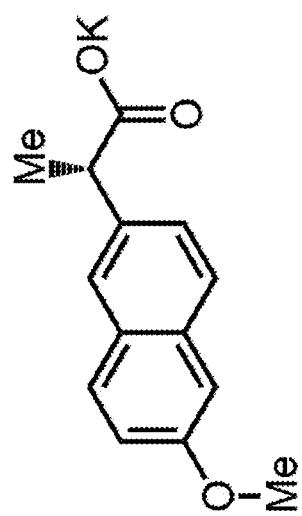
Figure 6:
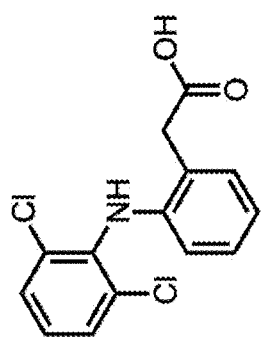

NSAIDs are examples of the types of anionic drug molecules that can be incorporated into CD-MOFs to form a pharmaceutical complex. Suitable NSAIDs include ibuprofen, naproxen, and aspirin. The structures of the free acid forms of these three drug molecules are shown in FIGS. 1C and FIG. 6. Other small molecule drugs that can be used include diclofenac and zidovudine, the structures of which are also shown in FIG. 6. Still others include salicyclic acid, salsalate, diflunisal, fenoprofen, flurbiprofen, dexibuprofen, ketoprofen, oxaprozin, dexketoprofen, loxoprofen, indomethacin, etodolac, aceclofenac, tolmetin, ketorolac, sulindac, clonixin, licofelone, mefenamic acid, fluflenamic acid, tolfenamic acid, and meclofenamic acid.

In one method of incorporating the anionic drug molecules into a CD-MOF, the anionic drug molecules undergo anionic exchange reactions with charge-balancing anions that are initially present in the CD-MOF structure. This aspect of the invention is based, at least in part, on the inventors' discovery that, the incorporation of the drug molecules takes place via an anion exchange reaction rather than the mere adsorption of the free acid form of the drug molecules onto the CD-MOF surface. Therefore, in order to achieve high loadings of the drug molecules in the CD-MOF, the absorption of the drug molecules needs to take place in an environment that facilitates the deprotonation of the free-acid form of the drug molecule. Such an environment can be achieved by using a water-soluble, polar organic solvent, such as ethanol, alone or mixed with other polar solvents or mixed with water. However, the polarity of the solvent should still be able to solubilize the drug molecules, without dissolving the CD-MOF and is also desirably non-toxic. By way of illustration, in some embodiments of the method, the solvent, which may be a solvent mixture, has a polarity relative to water of at least 0.50 (for example, ethanol has a polarity of 0.654 relative to water). This includes solvents having a polarity relative to water of at least 0.55 and solvents having a polarity relative to water of at least 0.6. Other suitable solvents include methanol, 1-propanol, 2-propanol, 1-butanol, 2-butanol, glycerin, ethylene glycol, benzyl alcohol, larger alcohol and mixtures thereof and mixtures of these with water.

One embodiment of a method of forming a pharmaceutical complex via anion exchange includes the steps of forming a solution of: the free acid form of an anionic drug molecule; a CD-MOF having charge-balancing anions in its superstructure; and a polar organic solvent that facilitates the deprotonation of the free acid form of the anionic drug molecule in solution; and allowing the anionic drug molecules to undergo anion exchange with the charge-balancing anions of the CD-MOF to provide a CD-MOF loaded with the deprotonated from of the drug molecules. Allowing the drug molecules to undergo anion exchange can entail, for example, simply leaving the solution undisturbed from a time sufficient to achieve the desired degree of anion exchange, as illustrated in Example 1.

Alternatively, the pharmaceutical complexes can be synthesized by co-crystallizing CD with the alkali metal salt form of a drug molecule in the presence of an organic alcohol, wherein the alkali metal cations of the salt act as the metal source for the formation of the MOF structure and the drug anions provide the charge-balancing anion. The crystallization can be carried out using, for example, a vapor diffusion technique in which a vapor-phase alcohol, such as methanol, ethanol, isopropanol, or acetone, is used to induce crystallization.

Both synthesis methods are able to provide pharmaceutical complexes with a high loading of the drug molecules. For example, NSAID drug loadings for drug molecules, such as ibuprofen, naproxen, and/or aspirin, of at least 10 wt. % can be achieved. This includes embodiments of the pharmaceutical complexes having a drug loading of at least 20. wt. %. By way of illustration, drug loadings in the range from 10 wt. % to 30 wt. %, including drug loadings in the range from 23 wt. % to 30 wt. %; and drug loadings of 26 wt. % to 30 wt. % can be achieved for ibuprofen and other small anionic drug molecules.

Once the pharmaceutical complexes have been crystallized, they can be isolated from solution using, for example, filtration and/or centrifugation and, optionally washed and allowed to dry. Then they can be formulated into a liquid or solid oral dosage from, such as a tablet, containing the pharmaceutical complexes, with or without suitable diluents, that is designed to disintegrate in a physiological environment, such as a mammalian (e.g., human) patient's mouth or along the gastrointestinal tract.

EXAMPLE 1

Ibuprofen/CD-MOF-1 Complex

This example illustrates the loading of ibuprofen within CD-MOF-1 by two pathways, co-crystallization and adsorption, and shows that it is experimentally possible to achieve loadings that match the theoretically-calculated capacity. Additionally, this example shows that the CD-MOF/ibuprofen drug formulation is non-toxic, and has been tested on mice in order to assess the oral bioavailability and pharmacokinetics against control samples containing the potassium salt of ibuprofen by measuring the concentration found in blood plasma samples over time. It was found that the CD-MOF based formulation results in the same rapid uptake of ibuprofen that is typically found for ibuprofen salts, but the CD-MOF based formulation resulted in a statistically-significant increase (over 2-fold) of the half-life of ibuprofen in blood plasma. These results suggest that the CD-MOF/ibuprofen formulation may be suitable dosings that provide both rapid and sustained pain relief In addition, the preparation of the CD-MOF based formulation by adsorption of the free-acid of ibuprofen into the framework is less rigorous than the production of ibuprofen salts, and the CD-MOF formulation does not appear to be as susceptible to atmospheric moisture as the potassium salt of ibuprofen, which is a reason that this ibuprofen derivative has yet to be used in commercial formulations in the form of a tablet, but is available in the form of a liquid-filled gelatin capsule.

Results and Discussion

Figure 2:
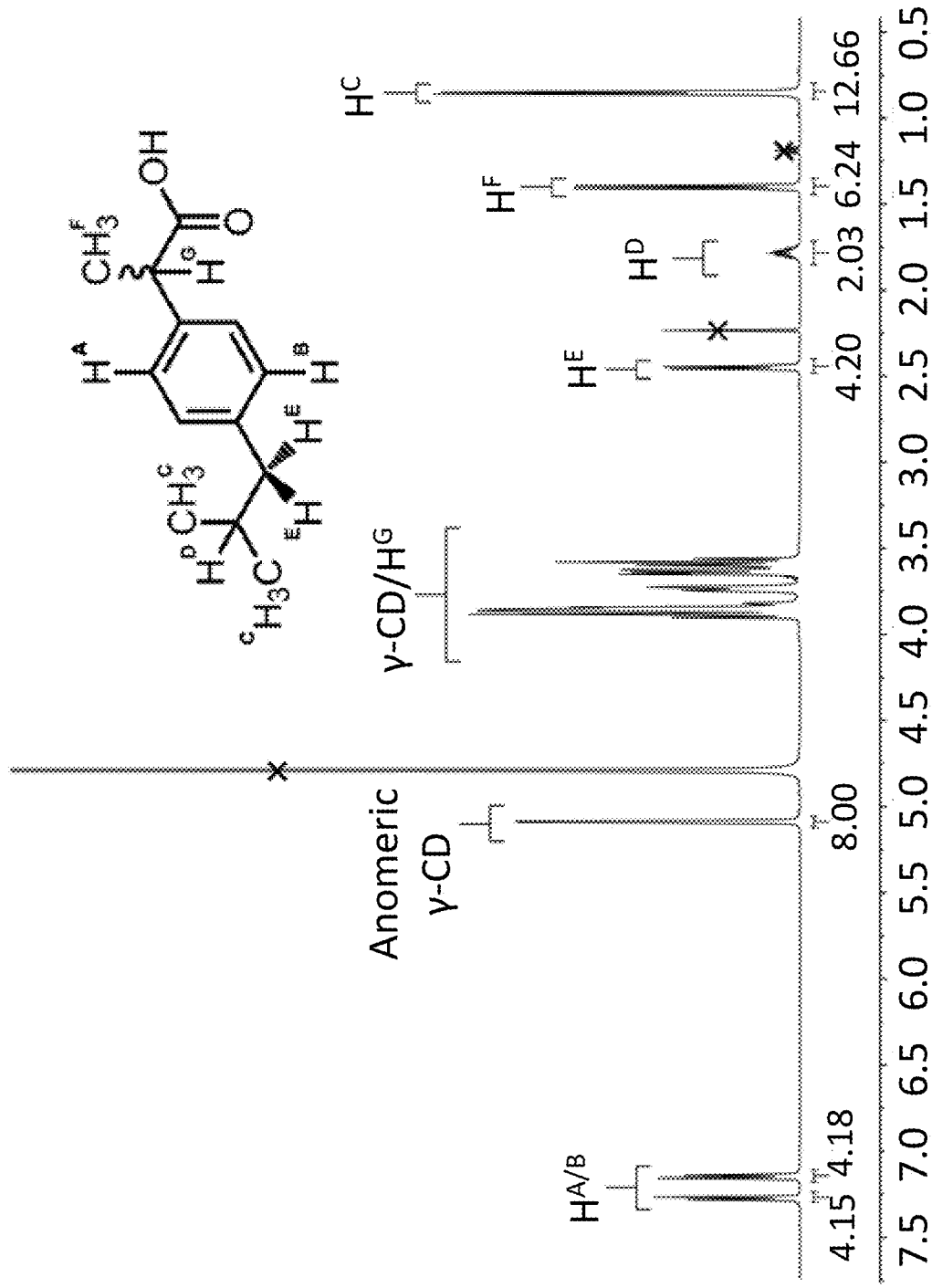
FIG. 2 shows the $^1H$ NMR spectrum (500 MHz, $D_2O$, 298 K) of CD-MOF-1 crystallized in the presence of the potassium salt of ibuprofen. Integration of the signals corresponding to the anomeric protons of γ-CD and the protons of ibuprofen reveal the presence of a 2:1 ratio of ibuprofen : γ-CD. Signals at 1.19 and 2.23 ppm correspond to residual EtOH and $Me_2CO$, respectively.
Figure 3A:
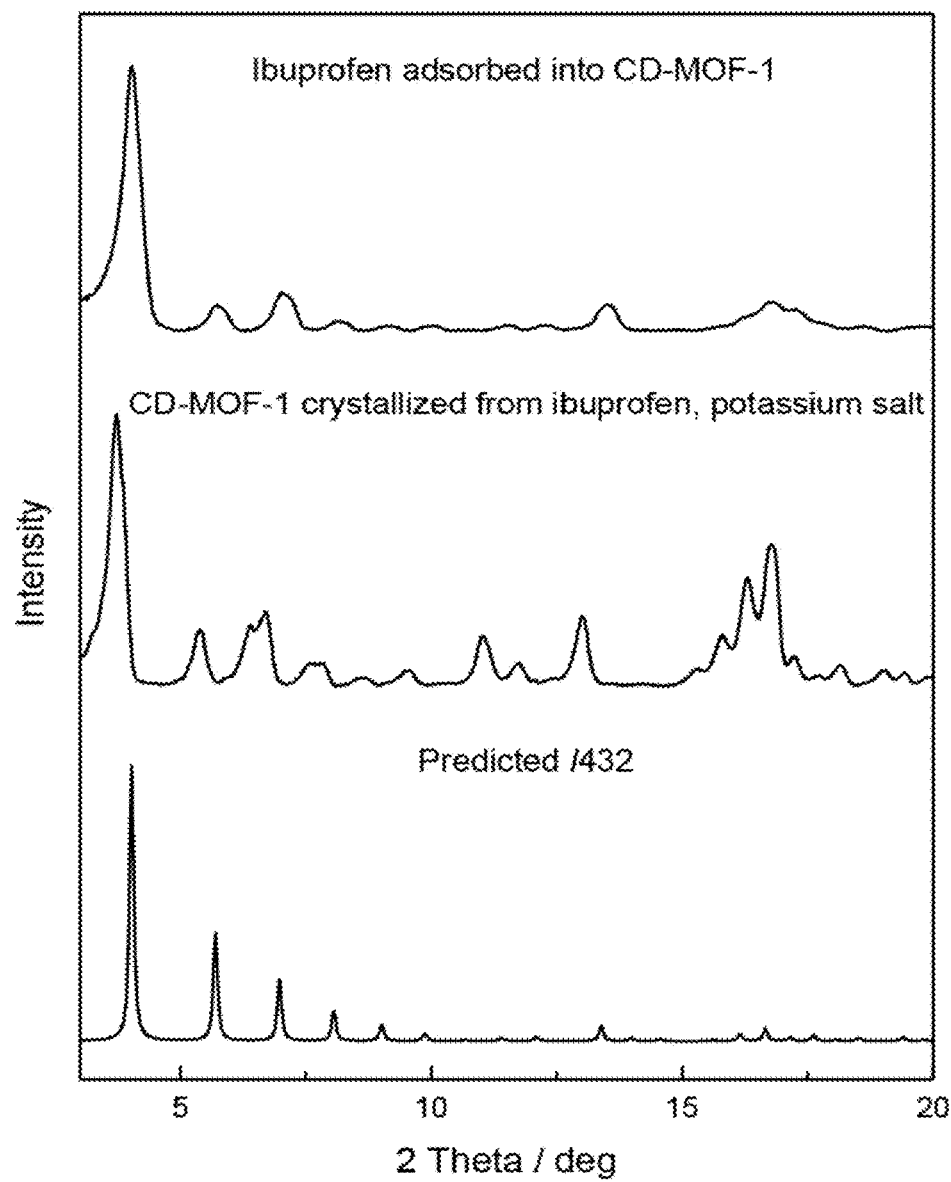
FIG. 3A depicts powder X-ray diffraction (PXRD) of freshly prepared CD-MOF-1 formulations of ibuprofen prepared by co-crystallization from the potassium salt of ibuprofen and adsorption of the deprotonated acid form of ibuprofen within a pre-existing CD-MOF-1, compared to the predicted I432 diffraction pattern.
Figure 3B:
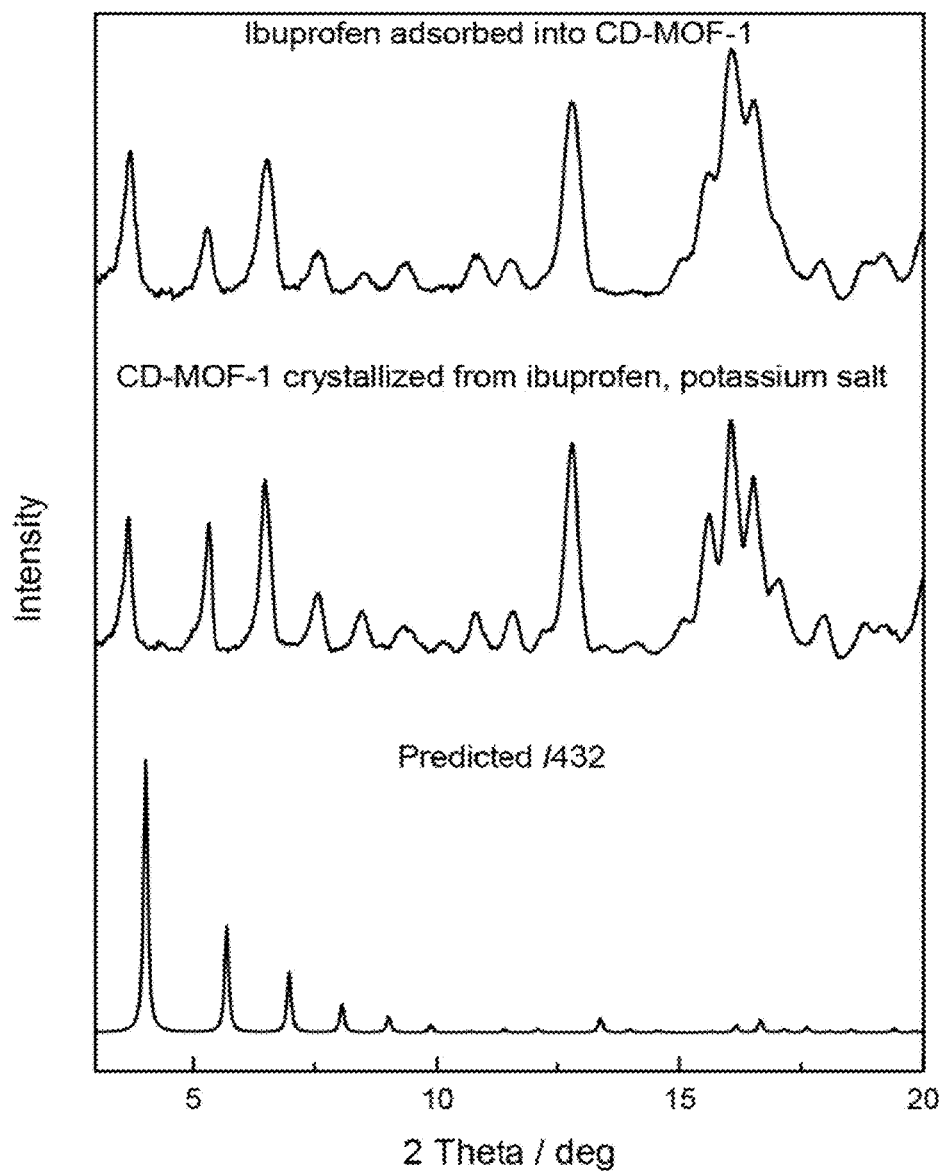
FIG. 3B depicts PXRD patterns of CD-MOF-1/ibuprofen formulations after storage in ambient conditions for three months, revealing that these samples retain their crystallinity over time.

Ibuprofen can be incorporated into CD-MOF-1 using two methods, (i) crystallization of CD-MOF using the potassium salt of ibuprofen as the source of alkali metal cations required to construct the framework, with charge balance achieved by the incorporation of ibuprofen anions and (ii) adsorption of the free-acid form of ibuprofen into CD-MOF-1. The first method is identical in principle to the synthesis of edible CD-MOF using potassium benzoate, and making use of EtOH diffusion into the aqueous solution in order to generate appropriate conditions for crystallization. In this case, two ibuprofen anions are expected per γ-CD ring and this is confirmed to be the case by using $^1$H NMR and comparing the integration of the signals corresponding to the anomeric proton of γ-CD to the signals corresponding to ibuprofen. (FIG. 2 shows the $^1$H NMR spectrum (500 MHz, $D_2O$, 298 K) of CD-MOF-1 crystallized in the presence of the potassium salt of ibuprofen.) This loading level equates to 23 wt. % of ibuprofen (as the anion) within CD-MOF. Furthermore, powder X-ray diffraction (PXRD) confirmed that the sample crystallized by diffusion of EtOH into an aqueous solution of γ-CD and the potassium salt of ibuprofen was indeed CD-MOF. (PXRD spectra for freshly prepared CD-MOF-1 formulations with ibuprofin and the same formulation after storage for 3 months are shown in FIGS. 3A and 3B, respectively.) This sample has crystallized in the R32 space group. Although large single crystals suitable for analysis by single-crystal X-ray diffraction were readily obtained, the ibuprofen anions could not be located within the porous framework as a result of a large amount of disorder in the structure.

The second approach relies on the crystallization of CD-MOF-1 using potassium hydroxide as the alkali metal source. For the purposes of preparing a pharmaceutical formulation, EtOH, rather than MeOH, was used to generate the conditions required for crystallization. After washing the prepared CD-MOF crystals with EtOH and drying under high vacuum at room temperature overnight, the crystals are suspended in a solvent containing ibuprofen in the free acid form, and this solution was left undisturbed for 5 days. The loading of ibuprofen within CD-MOF-1 was determined by dissolution of the crystals in 50 % v/v water : EtOH solution followed by analysis using UV-Vis absorption spectroscopy. It was found that the solvent that is used during the adsorption process is critical in controlling the amount of ibuprofen that is taken up by CD-MOF-1. When relatively non-polar solvents were used, the uptake of ibuprofen within CD-MOF-1 was low: approximately 5 wt. % ibuprofen is loaded within CD-MOF-1 using hexanes and $CH_2Cl_2$. When EtOH was used as the solvent during adsorption, however, the loading of ibuprofen within CD-MOF increased substantially to 26 wt. %, very close to what is predicted by Monte-Carlo simulations to be the maximum loading capacity of ibuprofen within CD-MOF (Bernini, M. C.; Fairen-Jimenez, D.; Pasinetti, M.; Ramirez-Pastor, A. J.; Snurr, R. Q., Screening of bio-compatible metal-organic frameworks as potential drug carriers using Monte Carlo simulations. *J. Mater. Chem. B* 2014, 2, 766-774).

In both of the loading scenarios that were tested, a racemic mixture of ibuprofen was used. The S-(+) enantiomer of ibuprofen is the pharmaceutically active isomer. However, the R-(–) enantiomer is not toxic, unlike other NSAIDs such as naproxen, and it can be metabolized such that it undergoes unidirectional chiral inversion to the S-(+) enantiomer. CD-MOF has the ability to resolve enantiomers using HPLC techniques (Bueno-Perez, R.; Martin-Calvo, A.; Gomez-Alvarez, P.; Gutierrez-Sevillano, J. J.; Merkling, P. J.; Vlugt, T. J. H.; van Erp, T. S.; Dubbeldam, D.; Calero, S., Enantioselective adsorption of ibuprofen and lysine in metal-organic frameworks. *Chem. Commun.* 2014, 50, 10849-10852). Circular dichroism experiments, however, show no enantioselectivity upon uptake of a racemic mixture of ibuprofen within CD-MOF using the loading conditions previously described. It is possible to crystallize and adsorb the pure enantiomers into CD-MOF, which gives similar loading results as the racemic mixture of ibuprofen. The use of the S-(+) enantiomer for commercial formulations has not been seen as necessary as a result of the low toxicity of the R-(–) enantiomer, the inversion of the R-(–) enantiomer to the pharmaceutically active enantiomer, and the additional cost associated with the resolution of enantiomers, either by separation or enantioselective synthesis.

Figure 4A:
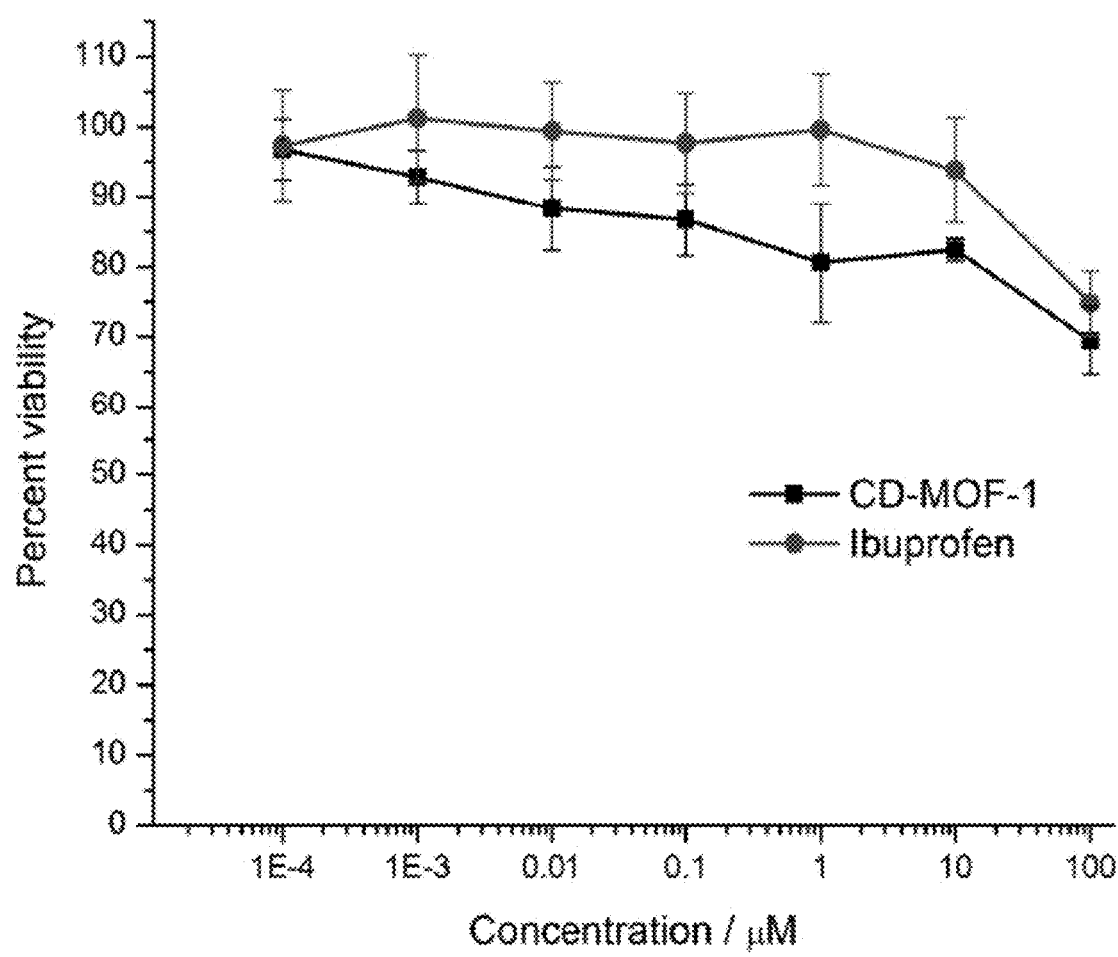
FIG. 4A depicts $IC_{50}$ studies of ibuprofen and CD-MOF-1 on MCF-10A cell lines.
Figure 4B:
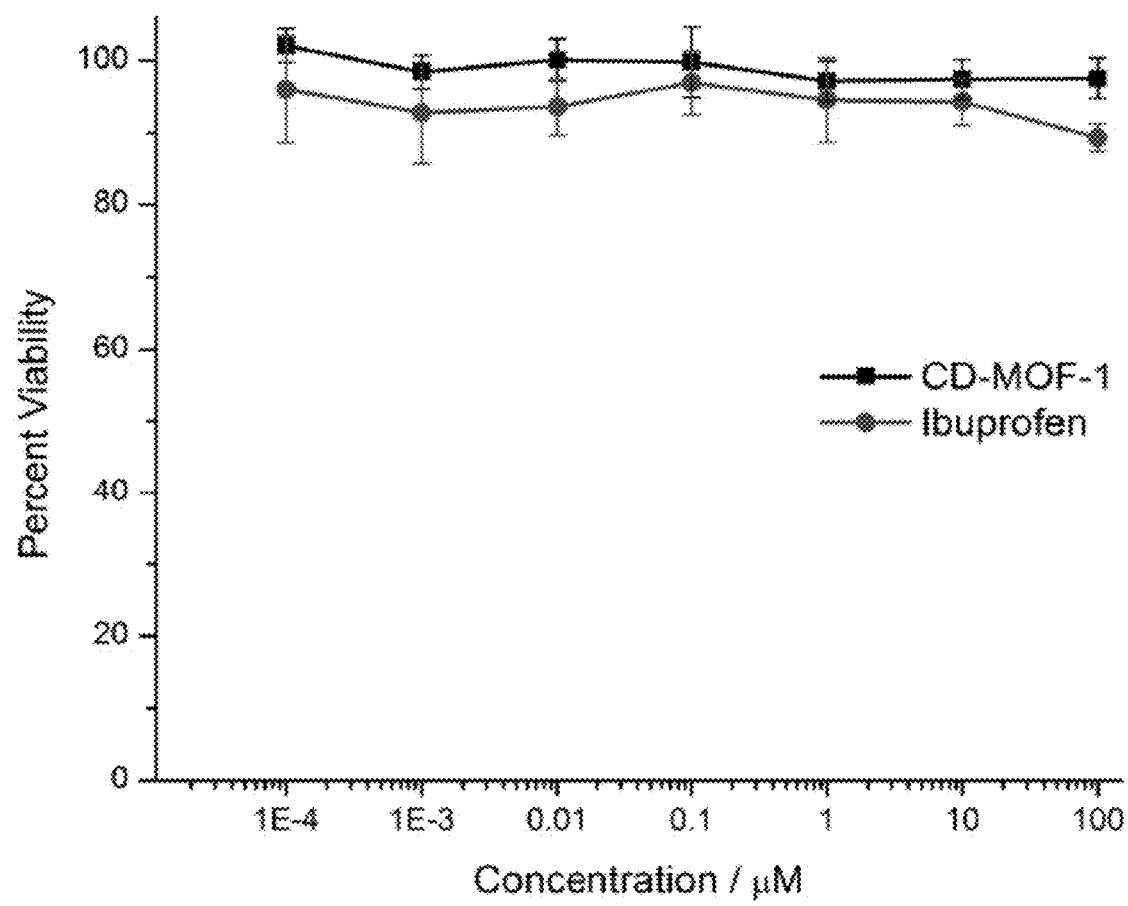
FIG. 4B depicts $IC_{50}$ studies of ibuprofen and CD-MOF-1 on MDA-MB-231 cell lines. For both samples tested, no $IC_{50}$ value could be determined up to a concentration of 100 μM.

Toxicity studies of both CD-MOF-1 and ibuprofen were carried out in vitro on two cell lines: MCF-10A (human mammary epithelial cells) (FIG. 4A) and MDA-MB-231 (human breast adenocarcinoma) (FIG. 4B). For both cell lines, no $IC_{50}$ value could be obtained for CD-MOF-1, and ibuprofen up to concentrations of 100 μM. This showed that CD-MOF-1 is not toxic, and formulations including CD-MOF-1 should be safe for animal studies.

Animal studies were conducted on 25 g female CD-1 IGS mice (Crl:CD1(ICR)), and the formulations were administered at a dose of 75 mg/kg ibuprofen by oral gavage using a suspension of the formulation in vegetable oil. Three mice per time point for each formulation were euthanized and blood samples were collected after 10, 20, 30, 45, 60, 90, 120 and 240 minutes, which were then centrifuged at 1500 rpm for 10 minutes at 4° C. to obtain plasma. Blood plasma samples were stored at –80° C. for transport for analysis by LC/MS.

Three formulations were tested: ibuprofen, potassium salt, and a physical mixture of 23 wt. % ibuprofen, potassium salt with γ-CD (which is analogous to a stoichiometric loading of ibuprofen within CD-MOF-1 created by co-crystallization) were used as control samples, and the third formulation contained CD-MOF-1 loaded with 26 wt. % ibuprofen by the adsorption protocol. The potassium salt of ibuprofen was considered to be the most appropriate control form of ibuprofen in this study, as the results of the solvent-dependent adsorption loading of ibuprofen is evidence that an anion exchange process was occurring within CD-MOf-1, i.e., deprotonation of the free-acid form of ibuprofen, which was facilitated by water-miscible polar solvents. In fact, this method of generating the potassium salt of ibuprofen is very simple, and results in a formulation that is stable under atmospheric conditions, unlike the potassium salt of ibuprofen alone which is very hygroscopic and, as such, is generally not used in pharmaceutical formulations in the form of a tablet. It is used, however, in rapid release gelatin capsules. After storage under ambient conditions after several months, the CD-MOF-1 formulation showed no signs of hygroscopicity, and the crystallinity of the porous extended framework was maintained.

Figure 5:
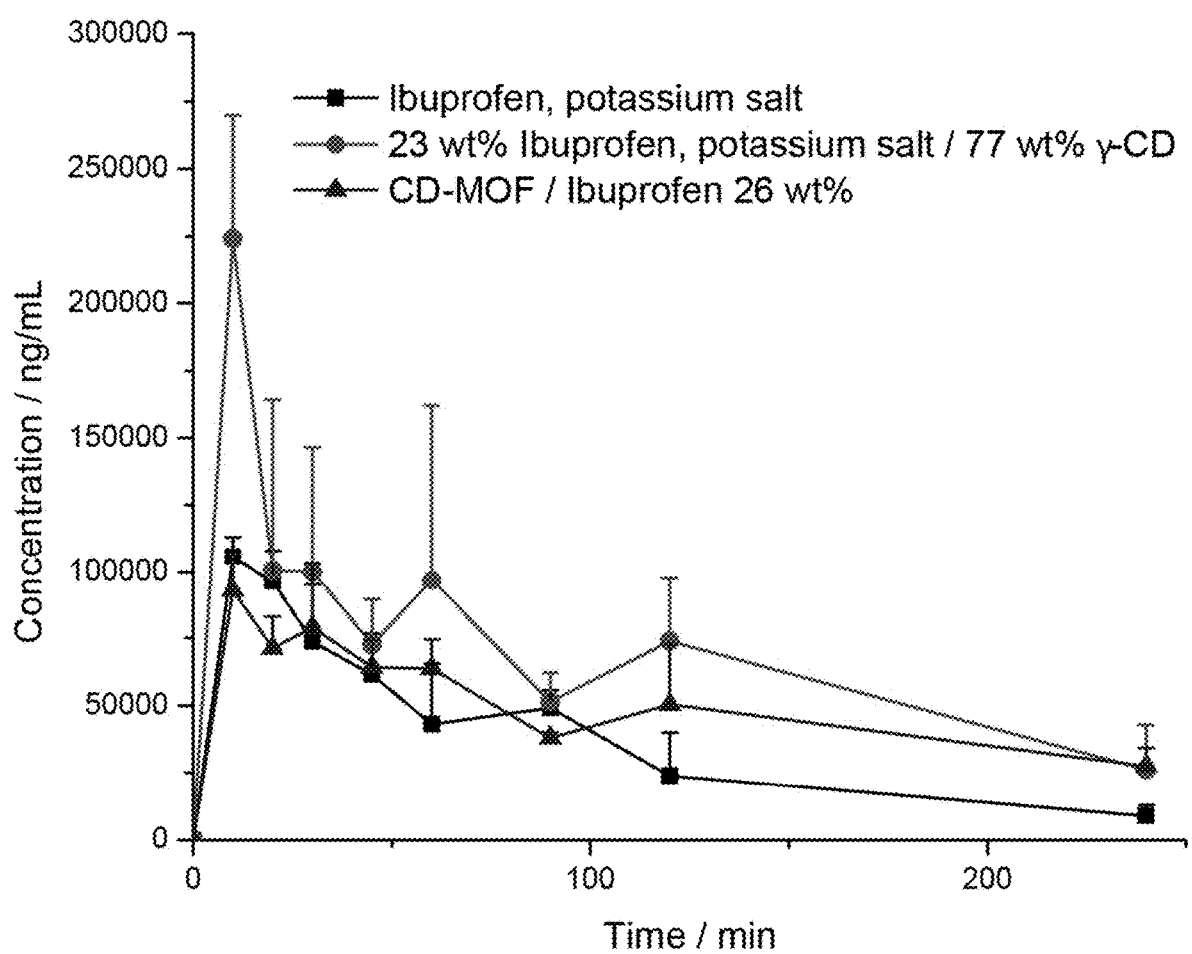
FIG. 5 shows pharmacokinetic data (n=3) for the three ibuprofen formulations tested in mice (25 g, 75 mg/kg) administered by oral gavage of a suspension of the formulation in vegetable oil (200 μL).

Pharmacokinetic data are shown in FIG. 5 and Table 1. The Microsoft Excel Add-in, PKSolver, was used to determine the pharmacokinetic parameters $C_{max}$, $T_{max}$, $AUC_{0-t}$, $AUC_{0-\infty}$ (area under the curve until the last time point and infinity, respectively) and the half-life ($t_{1/2}$), and results are reported as mean±standard deviation (Zhang, Y.; Huo, M.; Zhou, J.; Xie, S., PKSolver: An add-in program for pharmacokinetic and pharmacodynamic data analysis in Microsoft Excel. *Comput. Methods Programs Biomed.* 2010, 99, 306-314). One-way analysis of variance was carried out to evaluate the difference of the pharmacokinetic parameters between different formulations, followed by a Tukey's multiple comparison test in order to determine which means are statistically significantly different (P=0.05).

The maximum concentration of ibuprofen in plasma samples for all three formulations was reached rapidly, between 10-20 mins, which is ideal for analgesic drugs as this corresponds to a rapid onset of pain/inflammation relief. Unexpectedly, the control sample consisting of a physical mixture of 23 wt. % ibuprofen and potassium salt with γ-CD shows a statistically significant difference in the maximum concentration of ibuprofen. This would tend to suggest that γ-CD, or the byproducts of γ-CD hydrolysis, act(s) as an excipient for the absorption of ibuprofen, most likely by enhancing the solubility of ibuprofen after protonation in the digestive tract to the free-acid form. The bioavailability of ibuprofen, as measured by $AUC_{0-t}$ and $AUC_{0-\infty}$, is similar for all three formulations. However, the half-lives of the formulations containing γ-CD, as either the free molecule, or as part of CD-MOf-1, are statistically significantly longer than the potassium salt of ibuprofen alone. This illustrates the ability to provide a rapid acting formulation of ibuprofen that is also effective for long periods of time. Although the $AUC_{0-t}$ and $AUC_{0\infty}$ values for the formulations containing γ-CD were higher than for the pure potassium salt of ibuprofen, which would indicate greater bioavailability of ibuprofen in the formulations containing γ-CD (either as a free molecule or CD-MOF-1), they were not statistically significant (P=0.05) in this study.

Salts of ibuprofen are used in commercially available formulations, including the lysinate, arginate and sodium salts. These derivatives are typically more expensive than the free-acid form of ibuprofen, particularly the amino acid derivatives, but these derivatives all show faster rates of uptake than the free-acid form. The potassium salt is only used in liquid-filled gelatin capsules as a solution to the very hygroscopic nature of the potassium salt. Incorporation of the ibuprofen anion within CD-MOF-1 provides another solution to this problem. Given that it uses renewable and inexpensive ingredients, it is more cost-effective than what is currently available. Additionally, it could be used as a fast-dispersing formulation since γ-CD can be hydrolyzed by salivary α-amylase, which is another potential advantage over current liquid filled capsules.

Conclusion

This example shows that the NSAID ibuprofen can be incorporated within the porous architecture of CD-MOF in significant amounts. Although MOFs have been frequently discussed as potential drug-delivery vehicles, very few instances of in vivo studies involving MOFs have been reported to date. In this instance, CD-MOF-1 is a non-toxic, biocompatible MOF, and as a result of its construction from alkali metal cations, it was able to readily incorporate pharmaceutically-active anions within its extended structure. Pharmacokinetic data reveal that CD-MOF-1 formulations of the potassium salt of ibuprofen exhibit similar bioavailability and rapid uptake in blood plasma as the pure potassium salt of ibuprofen. The formulations that include the presence of γ-CD, however, appear to show a statistically significantly longer half-life than the formulation lacking γ-CD. These results demonstrate that CD-MOF-1 can be used as a delivery agent for NSAIDs to provide quick pain relief and extended duration of the analgesic effect. Furthermore, the ease of creating this formulation, by adsorption of the free-acid of ibuprofen within the framework, can be applied to create salts of other acid forms of NSAIDs such as naproxen, and other drug molecules that are difficult to work within their salt form. Given that CD-MOF-1 is constructed from γ-CD, other drug formulations based on CD-MOF-1 can exhibit the same advantages, as well as enhance the bioavailability of a wide range of poorly water-soluble drugs, and can even be used to generate solid formulations of liquid and oily APIs.

Methods

Incorporation of Ibuprofen within CD-MOF-1. Method 1: Potassium tert-butoxide (0.66 g, 5.8 mmol) was dissolved in PhMe (30 mL) and ibuprofen (1.2 g, 5.8 mmol) was added to the resulting solution with stirring, resulting in the formation of a highly viscous solution/gel. After 2 hr, the mixture was dried under high vacuum to remove all PhMe. The resulting white solid was dissolved in $H_2O$ (10 mL), and γ-CD (1.9 g, 1.5 mmol) was added. The solution was filtered through a 0.45 μm syringe filter (Pall) and exposed to EtOH vapor for at least 2 weeks. The subsequent crystals were washed with EtOH (3×20 mL) and dried under high vacuum overnight. Method 2. CD-MOF-1 (0.5 g), prepared according to procedures reported in the literature, was added to an ethanolic solution of ibuprofen (10 mL, 0.53 M), and the suspension was left undisturbed in the absence of light for 5 days. The crystals were washed with EtOH (3×50 mL) and dried under high vacuum overnight. The uptake of ibuprofen was determined by UV-Vis absorption spectroscopy, wherein a known quantity of the crystals were dissolved in a 50% EtOH:$H_2O$ solution and compared to a sample of the free-acid of ibuprofen dissolved in the same solvent mixture ($\varepsilon$=217 $M^{-1}cm^{-1}$ at 264 nm). Circular dichroism experiments were performed on aqueous solutions of the CD-MOF-1/ibuprofen formulations using a Jasco J-815 Circular Dichroism Spectrophotometer.

Cell Studies. For cell studies, CD-MOF-1 was solubilized in $H_2O$ and the free-acid of ibuprofen was solubilized in $Me_2SO$. The growth inhibition of various cell lines was determined according to the protocols from the NCI/NIH Developmental Therapeutics Program, and in collaboration with the Northwestern University Developmental Therapeutics Core Facility. Cells were plated in triplicate in 96 well plates. The cells were plated at densities of 10,000 per well in 90 µL for MDA-MB-231; and 25,000 per well in 90 µL for MCF-10A. The MDA-MB-231 cells were cultured in RPMI1640 media supplemented with 10% Fetal Bovine Serum (FBS), and 2 mM glutamine with 5% $CO_2$ at 37° C. For experiments, 5% of FBS and 50 µg/mL of gentamycin were used. The MCF-10A cells were cultured in DMEM/F12 with 5% horse serum, 20 ng/mL of EGF, 0.5 mg/mL hydrocortisone, 100 ng/mL cholera toxin, 10 µg/mL insulin and 1% penicillin/streptomycin. For experiments, the component was half of maintaining media. Following cell inoculation, the plates were incubated at 37° C., 5% $CO_2$, 95% air and 100% relative humidity for 24 hours.

Time zero cells (Tz) were processed according to the Promega Cell Titer Glo, and the following day Cell Titer-Glo Luminescent Cell Viability Assay. At 48 hours post-drug concentration treatment (10 µL of final drug volume added per well), all plates were allowed to equilibrate to room temperature from incubation for 30 min. 100 µL of activated Cell Titer Glo reagent was added to equal volumes of cell and drug media. The plates were shaken for 2 min and allowed to sit for activation prior to reading for 10 min. Plates were read on a BioTek reader using the luminescence program.

Pharmacokinetic Studies. Female mice (CD1, Crl:CD1 (ICR), 20-22 g, Charles River) were acclimated up to 5 days. The animals were dosed at 75 mg/kg (based on ibuprofen anion) by oral gavage of a suspension of the formulation in vegetable oil (200 µL). At each time point, three mice were euthanized. Blood was collected at 8 different points: 10, 20, 30, 45, 90, 120, and 240 mins post dosing. Blood samples were collected and placed in K-EDTA tubes, and the tubes were centrifuged at 1500 rpm for 10 mins at 4° C. The study was conducted in accordance of Northwestern guidelines. The concentration of ibuprofen in plasma samples was determined by LC/MS using the analytical services of Sanford Burnham Prebys Medical Discovery Institute (Orlando, Fla.). PKSolver was used to determine the relevant pharcokinetic parameters, and Minitab 17 was used for statistical analysis. One-way analysis of variance and Tukey's multiple comparison test were used to determine statistically different means between different formulations at a significance level P=0.05.

EXAMPLE 2

Naproxen/CD-MOF-1 Complex

This example illustrates the loading of naproxen molecules into CD-MOF-1 via the co-crystallization method and anion exchange methods.

Co-Crystallization: Naproxen (2.7 g, 11.6 mmol) was dissolved in toluene (100 mL), to which potassium tert-butoxide (1.3 g, 11.6 mmol) was added, with stirring, at room temperature (~23° C.). Over time, the solution became a viscous mixture, and toluene was subsequently removed under high vacuum. The residue (the potassium salt of naproxen) was then dissolved in water (60 mL) and γ-cyclodextrin (3.8 g, 2.9 mmol) was added to the solution. Upon dissolution of all the γ-cyclodextrin, the mixture was transferred to crystallization tubes and CD-MOF-1 was crystallized by a vapor diffusion technique, wherein the vapor of an alcohol, such as methanol, ethanol, isopropanol, or acetone vapor was used to induce crystallization. Crystals of CD-MOF-1 were formed after several days (the time depended on nature of vapor) and were washed with a mixture of water and the solvent used to induce crystallization. After washing, the crystals were dried under high vacuum and analyzed by NMR to confirm naproxen loading, and powder and single-crystal XRD to confirm the crystal structure of these CD-MOFs. The location of naproxen anions could not be found in single-crystal studies as a result of disorder within the pores of the framework.

The loading of naproxen within CD-MOF-1 was determined by dissolution of the crystals in 50% v/v water : EtOH solution followed by analysis using UV-Vis absorption spectroscopy at room temperature. The loading of ibuprofen within CD-MOF-1 was 32.5 wt. %.

Anion Exchange: The procedure for the adsorption, via anion exchange, of naproxen within CD-MOF-1 was identical to the procedure for the adsorption, via anion exchange, for ibuprofen, wherein the anion exchange took place in a 1 M ethanolic solution (5 mL) and the resulting solution was left undisturbed for 5 days. A racemic mixture of naproxen was used and both isomers were taken up by the CD-MOF-1. Therefore, it is advisable to begin with a pure solution of the S-(+)-naproxen, rather than the racemic mixture.

The loading of naproxen within CD-MOf-1, as determined by dissolution of the crystals in 50% v/v water : EtOH solution followed by analysis using UV-Vis absorption spectroscopy, was 11.4 wt. %. This reduced loading relative to ibuprofen can be explained by the larger size of the naproxen molecules, which cannot access the extended porous network the CD-MOF as readily.

EXAMPLE 3

IBuprofen/Channel Structure CD-MOF Complex

This example illustrates the synthesis of an offset channel structure CD-MOF having its γ-cyclodextrin tori linked to one another through alkali metal cations to form channels that are stacked in an offset manner down the crystallographic a-axis of the metal organic framework. This example also illustrates the loading of ibuprofen molecules into the offset channel structure CD-MOF via the adsorption and co-crystallization methods.

γ-Cyclodextrin (1.3 g, 1 mmol) and sodium carbonate (0.85 g, 8 mmol) were dissolved in water (20 mL). The solution was then transferred to crystallization tubes (5 mL solution in each tube) and crystallization of a metal organic framework was achieved by diffusion of methanol vapor over the period of 1 month. The majority of the crystals were washed with methanol and dried under high vacuum, and several crystals were set aside for analysis by single-crystal X-ray diffraction.

Figure 7:
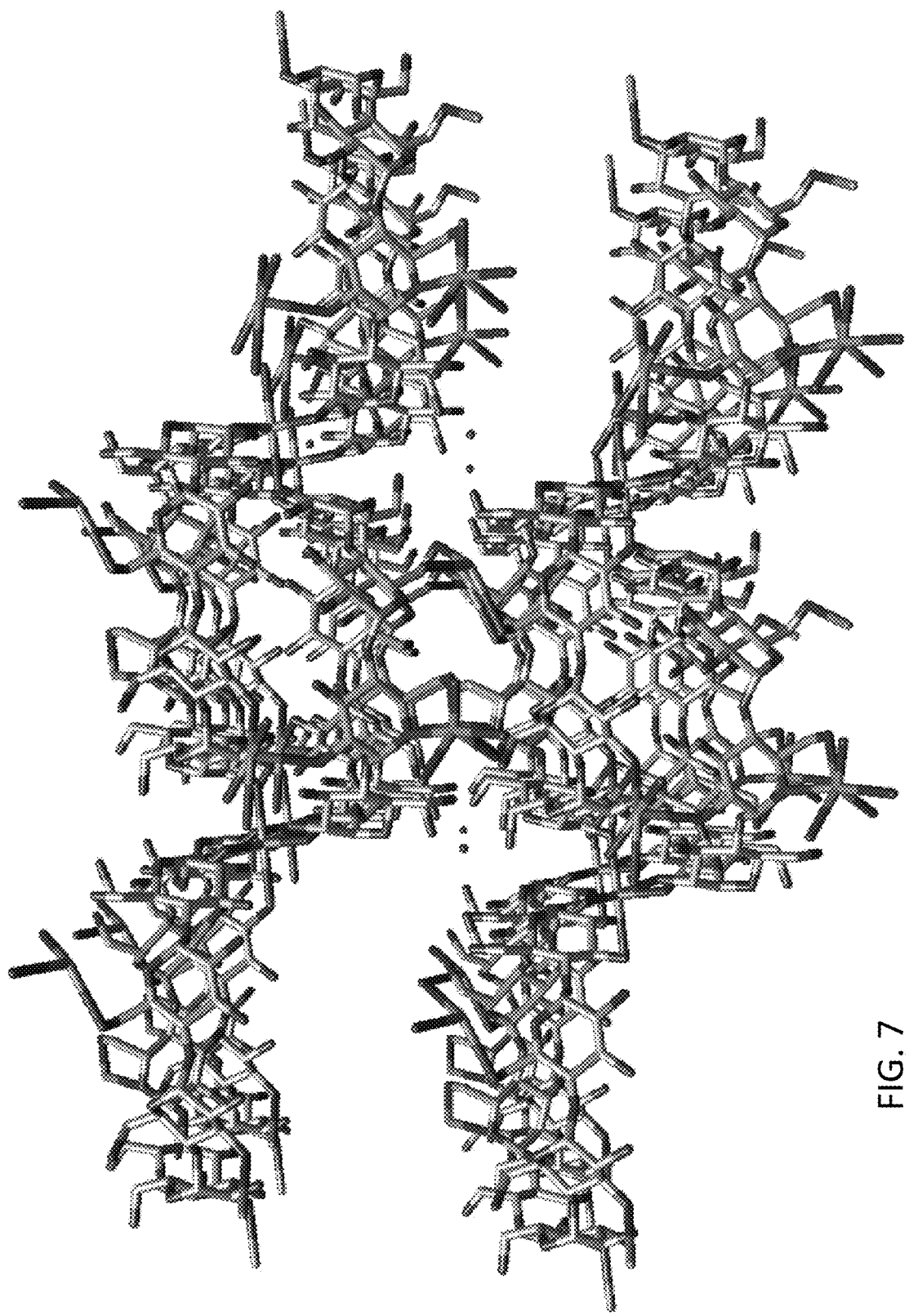
FIG. 7 shows the solid state structure of an offset channel structure CD-MOF.
Figure 8:
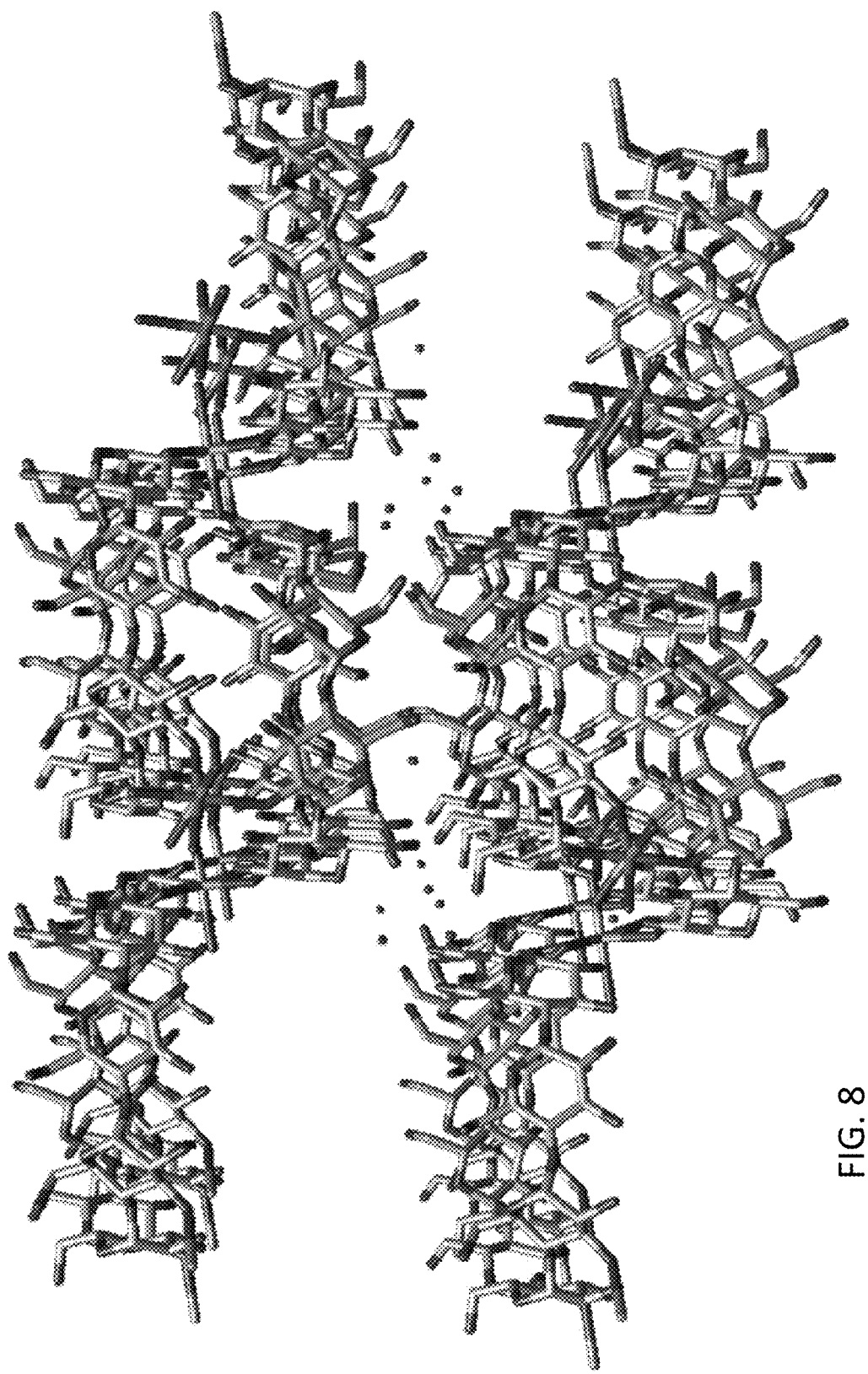
FIG. 8 shows the solid state structure $[(NaOH)_2 \cdot (\gamma\text{-}CD)]_n$.

Single-crystal X-ray diffraction revealed that the structure of this framework was almost identical to that reported previously in the case of the crystallization of γ-cyclodextrin with sodium hydroxide (CCDC number 853694), however, the previously reported structure is not considered to be a metal-organic framework (MOF) since coordination of γ-cyclodextrin to sodium cations is not extended throughout the entire structure. (Forgan et al., *J. Am. Chem. Soc.* 2012, 134, 406-417.) The solid-state structure of the single crystals that were grown using 8 equivalents of sodium carbonate showed an almost identical arrangement of γ-cyclodextrin. However, additional sodium cations were present in this structure and these coordinated to the primary face of the cyclodextrin, resulting in extended coordination of the cation to the macrocycle. As a result, this new structure can be considered a MOF. This new structure, which is shown in FIG. 7, includes three sodium cations for every two γ-cyclodextrin macrocycles, whilst the previously reported structure, which is shown in FIG. 8 for comparison, includes of two sodium cations for every two γ-cyclodextrin macrocycles.

Anion Exchange: The crystals (300 mg) that were dried under high vacuum were exposed to an ethanolic solution of ibuprofen (1 M, 5 mL) for five days, after which time the crystals were washed with ethanol (5×20 mL) to remove any excess ibuprofen, and then dried under high vacuum. Loading of ibuprofen within these crystals was determined by UV-Vis spectroscopy by dissolution of the crystals in a mixture of water and ethanol (50 vol. %). A loading of 16.9 wt. % of ibuprofen was found within this structure.

Co-Crystallization: Co-crystallization of γ-cyclodextrin (1.3 g, 1 mmol) and the sodium salt of ibuprofen (1.8 g, 8 mmol) in water (20 mL) using methanol vapor also yielded large crystals.

Although pharmaceutical complexes incorporating an offset channel structure MOF having sodium nodes is illustrated here, the same methods can be applied to yield offset channel structure MOF having different alkali metal cations, such as potassium, rubidium, or cesium at the nodes.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A pharmaceutical complex comprising:
a metal organic framework comprising γ-cyclodextrin tori coordinated to alkali metal cations on primary and secondary faces of the γ-cyclodextrin tori;
wherein the metal organic framework is an offset channel metal organic framework comprising γ-cyclodextrin tori linked to one another through the alkali metal cations to form channels that are stacked in an offset manner down the crystallographic a-axis of the metal organic framework and has the chemical formula $C_{96}H_{169}X_3O_{84.5}$, $3H_2O$, where X is an alkali metal element, and crystallizes in the P1 space group;
deprotonated drug molecules associated with the alkali metal cations as charge-balancing anions; and
wherein the pharmaceutical complex has a drug molecule loading of at least 10 wt. %.

2. The complex of claim 1, wherein the alkali metal element is Na.

3. The complex of claim 1, wherein the alkali metal element is K.

4. The complex of claim 1, wherein the deprotonated drug molecules are deprotonated ibuprofen molecules.

5. The complex of claim 2, wherein the deprotonated drug molecules are deprotonated ibuprofen molecules and the pharmaceutical complex has an ibuprofen loading of at least 20 wt. %.

6. The complex of claim 1, wherein the deprotonated drug molecules are deprotonated naproxen molecules or deprotonated aspirin molecules.

7. The complex of claim 2, wherein the deprotonated drug molecules are deprotonated naproxen molecules or deprotonated aspirin molecules.

8. The complex of claim 1, wherein the metal organic framework is CD-MOF-3 comprising six γ-cyclodextrin tori that are coordinated to cesium cations on the primary face of the cyclodextrin tori in an alternating manner, forming cubes, wherein the cubes are linked together in three dimensions by coordination of a cesium cation on the secondary face of the γ-cyclodextrin tori, leading to an extended porous superstructure.

9. A solution comprising the complex of claim 1 in a water-soluble, polar organic solvent, wherein the drug molecule has a free-acid form and the water-soluble, polar organic solvent facilitates the deprotonation of the free-acid form of the drug molecule.

10. A pharmaceutical complex comprising:
an offset channel metal organic framework comprising γ-cyclodextrin tori linked to one another through the alkali metal cations to form channels that are stacked in an offset manner down the crystallographic a-axis of the metal organic framework and has the chemical formula $C_{96}H_{169}X_3O_{84.5}$, $3H_2O$, where X is an alkali metal element, and crystallizes in the P1 space group; and
deprotonated drug molecules associated with the alkali metal cations as charge-balancing anions.

11. The complex of claim 10, wherein the alkali metal element is Na.

12. The complex of claim 10, wherein the alkali metal element is K.

13. The complex of claim 10, the pharmaceutical complex has an drug molecule loading of at least 10 wt. %.

14. The complex of claim 10, the pharmaceutical complex has an drug molecule loading of at least 20 wt. %.

15. The complex of claim 10, wherein the deprotonated drug molecules are deprotonated ibuprofen molecules.

16. The complex of claim 10, wherein the deprotonated drug molecules are deprotonated naproxen molecules or deprotonated aspirin molecules.

17. A solution comprising the complex of claim 10 in a water-soluble, polar organic solvent, wherein the drug molecule has a free-acid form and the water-soluble, polar organic solvent facilitates the deprotonation of the free-acid form of the drug molecule.

18. A method of forming a pharmaceutical complex, the method comprising:
forming a solution comprising the free-acid form of acidic drug molecules and metal organic frameworks in a water-soluble, polar organic solvent, wherein the metal organic frameworks comprise γ-cyclodextrin tori coordinated to alkali metal cations on primary and secondary faces of the γ-cyclodextrin tori and further comprises charge compensating anions associated with the alkali metal cations, wherein the metal organic framework is an offset channel metal organic framework comprising γ-cyclodextrin tori linked to one another through the alkali metal cations to form channels that are stacked in an offset manner down the crystallographic a-axis of the metal organic framework and has the chemical formula $C_{96}H_{169}X_3O_{84.5}$, $3H_2O$, where X is an alkali metal element, and crystallizes in the P1 space group, and further wherein the polar organic solvent facilitates the deprotonation of the free-acid form of the acidic drug molecules; and allowing the deprotonated acidic drug molecules to undergo anion exchange with the charge compensating anions of the metal organic frameworks to form metal organic frameworks loaded with deprotonated acidic drug molecules.

19. A method of forming a pharmaceutical complex, the method comprising:

forming a solution comprising an alkali metal salt of a drug molecule, γ-cyclodextrin, and an organic alcohol; and co-crystallizing the alkali metal salt of the drug molecule and the γ-cyclodextrin in the presence of the organic alcohol to form a metal organic framework comprising γ-cyclodextrin tori coordinated to alkali metal cations on primary and secondary faces of the γ-cyclodextrin tori, wherein the metal organic framework is an offset channel metal organic framework comprising γ-cyclodextrin tori linked to one another through the alkali metal cations to form channels that are stacked in an offset manner down the crystallographic a-axis of the metal organic framework and has the chemical formula $C_{96}H_{169}X_3O_{84.5b1}$, $3H_2O$, where X is an alkali metal element, and crystallizes in the P1 space group, wherein the drug molecules are associated with the alkali metal cations as charge-balancing anions.

* * * * *

UNITED STATES PATENT AND TRADEMARK OFFICE
CERTIFICATE OF CORRECTION

PATENT NO. : 10,500,218 B2
APPLICATION NO. : 15/350975
DATED : December 10, 2019
INVENTOR(S) : Karel J. Hartleib et al.

Page 1 of 1

It is certified that error appears in the above-identified patent and that said Letters Patent is hereby corrected as shown below:

In the Specification

Column 2, Line 48, "$HJ_{169}$" should be --$H_{169}$--.

Column 9, Line 7, "MOf" should be --MOF--.

Column 9, Line 49, "MOf" should be --MOF--.

Column 12, Line 22, "MOf" should be --MOF--.

In the Claims

Column 15, Claim 19, Line 27, "$C_{96}H_{169}X_3O_{84.5bl}$ , $_3H_2O$" should be --$C_{96}H_{169}X_3O_{84.5},3H_2O$--.

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*